United States Patent [19]

Yoshigi et al.

[11] Patent Number: 5,726,057
[45] Date of Patent: Mar. 10, 1998

[54] BARLEY β AMYLASE STRUCTURAL GENE

[75] Inventors: Naohiro Yoshigi; Yukio Okada, both of Yaizu, Japan

[73] Assignee: Sapporo Breweries Limited, Tokyo, Japan

[21] Appl. No.: 737,597

[22] PCT Filed: Mar. 27, 1996

[86] PCT No.: PCT/JP96/00799

§ 371 Date: Nov. 25, 1996

§ 102(e) Date: Nov. 25, 1996

[87] PCT Pub. No.: WO96/30525

PCT Pub. Date: Oct. 3, 1996

[30] Foreign Application Priority Data

Mar. 27, 1995 [JP] Japan ................................ 7-092004

[51] Int. Cl.⁶ ............................ C12N 15/56; C12N 15/63
[52] U.S. Cl. ...................... 435/320.1; 536/23.2; 435/200
[58] Field of Search ......................... 536/23.2; 435/320.1, 435/200

[56] References Cited

PUBLICATIONS

Yoshigi, N., et al. (1995) Biosci. Biotech. Biochem. 59(10), 1991–1993.

Yoshigi, N., et al. (1995) J. Biochem. 118(3), 562–567.

Yoshigi, N., et al. (1995) J. Biochem. 117(1), 63–67.

Okada, Y., et al. (1995) Biosci. Biotech. Biochem. 59(6), 1152–1153.

Yoshigi, N., et. al. (1994) J. Biochem. 115(1), 47–51.

*Primary Examiner*—Charles L. Patterson, Jr.
*Attorney, Agent, or Firm*—Oblon, Spivak, McClelland, Maier & Neustadt, P.C.

[57] ABSTRACT

The present invention provides a barley β-amylase structural gene consisting of the nucleotide sequence shown in SEQ. ID. No. 1 in attached sequence listing, a barley β-amylase structural gene consisting of the nucleotide sequence shown in SEQ. ID. No. 2 in attached sequence listing, and a plasmid containing the nucleotide sequence shown in SEQ. ID. NO. 1 or 2 in attached sequence listing. The present invention can be utilized in breeding of barley and other plants and industrial production of β-amylase and can contribute in the technical fields of plant breeding, production of brewed products such as beer, production of distilled liquors, food production and enzyme industry.

3 Claims, 1 Drawing Sheet

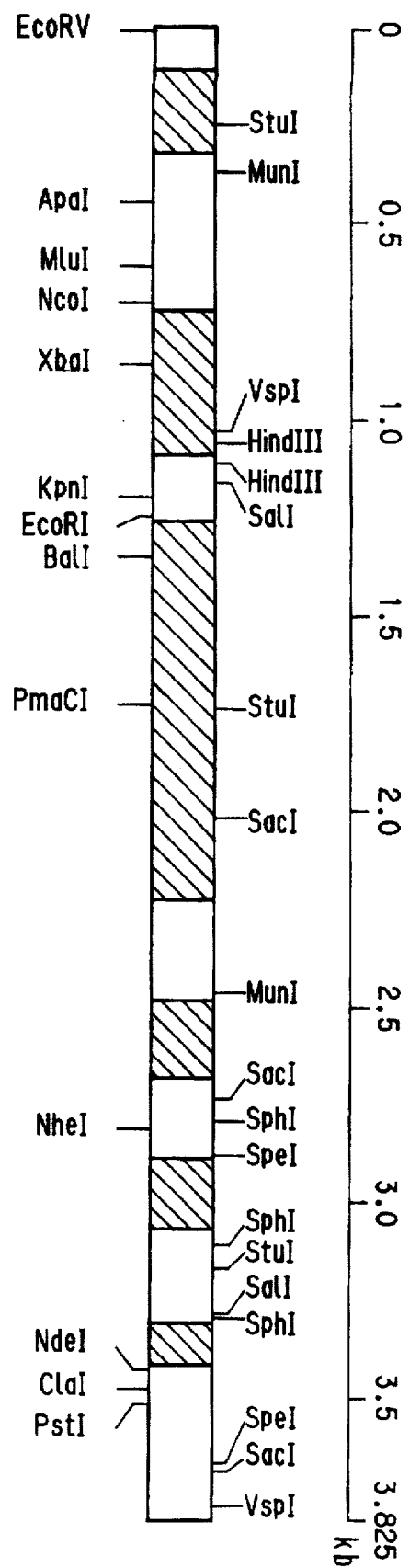
FIGURE

BARLEY β AMYLASE STRUCTURAL GENE

FIELD OF TECHNOLOGY

The present invention relates to barley β-amylase structural genes, to β-amylase genes subjected to nucleotide substitution in order to allow amino acid replacements effective for enhancement of heat stability of β-amylase, and to plasmids containing such genes.

BACKGROUND TECHNOLOGY

β-Amylase (α-1,4-glucan maltohydrolase; EC 3.2.1.2) catalyzes the liberation of β-maltose from the nonreducing ends of starch and related 1,4-α-glucans. The enzyme has been purified from various higher plants, e.g. barley and soybean, and microorganisms, and it is a major protein in the starchy endsperm of ungerminated barley seeds.

Barley β-amylase and soybean β-amylase are known as an enzyme useful in industrial production of maltose for infusion and food.

Barley malt is also known to be used as one of materials for beer or distilled liquors, and β-amylase in the malts is known as one of the most important enzymes for saccharification of starch at the mashing stage.

As a structural gene of barley β-amylase, a full length cDNA consisting of 1754 bases of cultivar Hiproly was reported, and it was coded for a polypeptide of 535 amini acids (Eur. J. Biochem., 169, 517 (1987)). A full length cDNA consisting of 1775 nucleotide cultivar of Haruna NIJO (two-rows) was also reported, and it was coded for a polypeptide of 535 amini acids (J. Biochem., 115, 47 (1994), Japanese Patent Kokai Hei 6-303983).

In the study of β-amylase of cultivar Haruna NIJO, an expression vector (pBETA92) was constructed by deleting 5'-terminal 55 base pairs of the full length cDNA and ligating a SmaI linker to form a DNA which was then inserted into the SmaI site of a plasmid pKK 223-3 (produced by Pharmacia Biotech).

Also by transforming this expression vector into *Escherichia coli* JM 109 (produced by Toyoho), recombinant β-amylase was produced. Recombinant β-amylase consisted of 531 amino acids, and had almost the same properties as β-amylase from barley (Biosci. Biotech. Biochem., 58, 1080 (1994), Japanese Patent Kokai Hei 6-303983).

However, it is not satisfactory that recombinant β-amylase had almost same properties as β-amylase from barley, since soybean β-amylase is employed more frequently in practice than barley β-amylase because of somewhat higher heat stability of the former. Accordingly, in order to enhance the utility of barley-derived recombinant β-amylase, its thermostability at least equivalent to that of soybean β-amylase should be needed.

As an example of β-amylases whose heat stability was enhanced by protein engineering, sevenfold-mutant β-amylase in which methionine at 181 position of the original recombinant β-amylase is replaced with leucine, serine at 291 position with alanine, isoleucine at 293 position with valine, serine at 346 position with proline, serine at 347 position with proline, glutamine at 348 position with aspartic acid and alanine at 372 position with serine was proven to have the thermostability higher than that of the original recombinant β-amylase (Japanese Patent Kokai Hei 6-233086). The original recombinant β-amylase lacked four amino acids at positions 2–5 in comparison with the presumed amino acid sequence of barley β-amylase. Therefore, amino acid positions described above correspond to amino acid positions higher by four in barley β-amylase(Biosci. Biotech. Biochem., 58, 1080 (1994), Japanese Patent Kokai Hei 6-303983).

Barley β-amylase genes are only known to be present not only on the short arm of chromosome 2 but also on the long arm of chromosome 4 (Genet. Res. Camb., 51, 13 (1988)). But no studies of the isolation and sequence of a nuclear gene encoding β-amylase have been reported to data.

Furthermore, new technique of genetic manipulation will be applied in addition to conventional mating methods in the field of breeding barley cultivars, and β-amylase gene is considered to be a candidate of the genes to be introduced to barley cells (Brewers' Guardian, 123, 31 (1994)).

When considering mass production of β-amylase gene in barley or expression in other plants, not only the β-amylase cDNA which has already been isolated but also a nuclear gene containing introns must be a leading candidate of the gene to be introduced because of the following reason. In chromosomal DNA of an eucaryote there are intervening sequences called as introns which are spliced when converted into a mature mRNA and thus are not present in a mature mRNA, and there is a possibility that these introns play an important role in the expression of a large amount of β-amylase in barley or the expression on other plants. It was reported that, especially in the plants such as rice, by using a gene containing an intron, the amount of the expression in a plant cell was increased by 10 times or more ("Creation of dream plants", TOKYO KAGAKU DOJIN, page 57 (1994)).

The present invention was established in view of the subject mentioned above, and the object of the invention is to isolate the barley β-amylase structural gene containing introns and to provide a plasmid comprising such gene. It is another object of the invention to construct a gene in which nucleotide substitutions capable of causing amino acid replacements serving to enhance heat stability of β-amylase is introduced by site-directed mutagenesis, whereby providing a plasmid containing such gene.

The present inventors made much effort to isolate barley β-amylase structural gene containing introns to which the method of enhancing heat stability disclosed in the former patent application (Japanese Patent Kokai Hei 6-233086) (i.e. introduction of nucleotide substitutions by site-directed mutagenesis causing amino acid replacements serving to enhance heat stability of β-amylase) is applied, and as a result the present invention is established.

Thus, according to the present invention, barley β-amylase structural gene containing introns can be sequenced, and can be expressed in a large amount in barley or can be expressed also in plants other than barley while ligating appropriate promoter or transcription terminator to this gene, whereby being utilized to breed barley or other plants.

In addition, the present invention enables expression of β-amylase having enhanced heat stability in barley or other plants by ligating an appropriate promoter or transcription terminator to Barley β-amylase gene in which amino acid replacements serving to enhance heat stability has occurred, whereby being utilized to breed barley or other plants.

DISCLOSURE OF THE INVENTION

The first aspect of the present invention is a barley β-amylase structural gene consisting of the nucleotide sequence shown in SEQ. ID. No. 1 in attached sequence listing.

The second aspect of the present invention is a barley β-amylase structural gene consisting of the nucleotide sequence shown in SEQ. ID. No. 2 in attached sequence listing.

The third aspect of the present invention is a plasmid containing the nucleotide sequence shown in SEQ. ID. NO. 1 or 2 in attached sequence listing.

BRIEF DESCRIPTION OF DRAWINGS

FIGURE 1 shows a physical map of a barley β-amylase structural gene containing introns.

BEST MODE TO PRACTICE THE INVENTION

Practical procedures to construct barley β-amylase structural genes, genes coding barley β-amylase having enhanced heat stability and plasmids containing such genes are described below.

(1) Preparation of barley chromosomal DNA

Barley seeds are germinated in darkness at 20° C. for 7 days in vermiculite. From young leaves chromosomal DNA can be isolated in a known manner, for example, by the method described in "Cloning and sequence—Plant biotechnology experiment manual" (NOSON BUNKASHA, page 252 (1989)).

(2) Cloning of barley β-amylase structural gene

The barley β-amylase structural gene can be cloned using Ex Taq kit (produced by Takara Shuzo). DNA obtained is ligated with various linkers or adapters using DNA ligases or, alternatively, a restriction enzyme site has previously been introduced in primers and amplified DNA is digested with the restriction enzyme, and then inserted into an appropriate plasmid to construct a recombinant DNA.

As a host microorganism, any of those in which the recombinant DNA can be kept stably and which can proliferates spontaneously may be employed. For example, *Escherichia coli* may be employed.

The recombinant DNA may be transfered into the host microorganism by a known method, for example, employing competent cell method (J. Mol. Biol., 53, 159 (1970)) when the host microorganism is *Escherichia coli*.

(3) Nucleotide sequencing

DNA sequencing can be done using the chemical modification method by MAXAM-GILBERT (Methods in Enzymology, 65, 499 (1980)) or the dideoxy method (Gene, 19, 269 (1982)).

The barley β-amylase amino acid sequence can be deduced from the nucleotide sequence determined as described below.

(4) Nucleotide substitution in β-amylase structural gene

The nucleotide substitutions can be done by site-directed mutagenesis (Anal. Biochem., 200, 81 (1992)).

In order to utilize the barley β-amylase structural gene in breeding, a plasmid containing said gene is constructed and introduced into barley or other plants according to a standard manner. To introduce any gene into plant cell directly, any of known methods such as electroporation, polyethylene glycol method, particle gun method, laser puncture method and the like may be employed. As described above, the present invention relates to the barley β-amylase structural gene which can be utilized in plant breeding and industrial manufacturing of β-amylase, and thus is very useful in the technical fields of plant breeding, production of brewed products such as beer, production of distilled liquors, food production and enzyme industry.

EXAMPLE

The present invention is further described in the following examples, by which the present invention is not restricted in any way.

Example 1

Preparation of Barley Chromosomal DNA

About 1000 barley seeds (Haruna NIJO) were germinated in darkness at 20° C. for 7 days in vermiculite. Young leaves obtained (about 65 g) were cut into pieces of about 1 cm, from which then chromosomal DNA was prepared. As a result, about 1 mg of DNA was isolated from 10 g of the ypung leaves.

Example 2

Cloning of Barley β-amylase Structural Gene

Polymerase chain reaction (PCR) amplification was used. The reaction mixture contained 10 μg of DNA, 20 pmol of each primer, 2.5 mM of dNTP, and 2.5 units of Ex Taq DNA polymerase. The 5'-end primer sequence was shown in SEQ. ID. No. 3 in the sequence listing and the 3'-end primer sequence was shown in SEQ. ID No. 4 in the sequence listing.

The restriction map of the DNA obtained by PCR amplification is shown in FIGURE 1. Open boxes and the boxes with oblique lines indicate exon and intron, respectively.

Example 3

β-amylase Structural Gene Nucleotide Sequencing

DNA obtained was digested with various restriction enzymes and were subcloned into pUC 118 and pUC 119 for DNA sequencing. DNA sequencing was done using the dideoxy method (See SEQ. ID. No. 1 in the sequence listing).

The structural gene was 3825 base pairs in length. In the sequence of the structural gene, a sequence identical to that of the cDNA (J. Biochem., 115, 47 (1994), Japanese Patent Kokai Hei 6-303983) was found to contain seven exons and six introns.

Nucleotide sequence of the structural gene and deduced amino acids are shown below (SEQ ID No. 1 and 10). Small letters indicate the sequences of introns, and the intron sequences are boxed. Asterisks mark a stop codon.

| | |
|---|---|
| GATATCCAACAAACCATTTGAAGTTGTAGAGCATCATCCATAGCCAGCATCCACAATGGA | 60 |
| Met G1 | |

| | |
|---|---|
| GGTGAACGTGAAAGGCAACTATGTCCAAGTCTACGTCATGCTCCCTgtaagctccatcca | 120 |
| u Val Asn Val Lys Gly Asn Tyr Val Gln Val Tyr Val Met Leu Pro | |
| ttcagaccaatcgctgagaaccacacactaaaactatttcaaggatctagtgcacacata | 180 |
| tacattattgttgtacatataacattgatacttcttgtaaaactctaattcaaagggtga | 240 |
| agaacaagatctgaggcctcaaatgagtatttatttgtactaaccttgactacacttcc | 300 |
| attgttgaaataaataaataagCTGGACGCCGTGAGCGTGAACAACAGGTTCGAGAAGGGC | 360 |

-continued

```
                    Leu Asp Ala Val Ser Val Asn Asn Arg Phe Glu Lys Gly
GACGAGCTGAGGGCGCAATTGAGGAAGCTGGTAGAGGCCGGTGTGGATGGTGTCATGGTA         420

Asp Glu Leu Arg Ala Gln Leu Arg Lys Leu Val Glu Ala Gly Val Asp Gly Val Met Val
GACGTCTGGTGGGGCTTGGTGGAGGGCAAGGGCCCCAAGGCGTATGACTGGTCCGCCTAC         480

Asp Val Trp Trp Gly Leu Val Glu Gly Lys Gly Pro Lys Ala Tyr Asp Trp Ser Ala Tyr
AAGCAGTTGTTTGAGCTGGTGCAGAAGGCTGGGCTGAAGCTACAGGCCATCATGTCGTTC         540

Lys Gln Leu Phe Glu Leu Val Gln Lys Ala Gly Leu Lys Leu Gln Ala Ile Met Ser Phe
CACCAGTGTGGTGGCAACGTCGGCGACGCCGTCAACATCCCAATCCCACAGTGGGTGCGG         600

His Gln Cys Gly Gly Asn Val Gly Asp Ala Val Asn Ile Pro Ile Pro Gln Trp Val Arg
GACGTCGGCACGCGTGATCCCGACATTTTCTACACCGACGGTCACGGGACTAGGAACATT         660

Asp Val Gly Thr Arg Asp Pro Asp Ile Phe Tyr Thr Asp Gly His Gly Thr Arg Asn Ile
GAGTACCTCACTCTTGGAGTTGATAACCAGCCTCTCTTCCATGGAAGATCTGCCGTCCAG         720
Glu Tyr Leu Thr Leu Gly Val Asp Asn Gln Pro Leu Phe His Gly Arg Ser Ala Val Gln
```

```
gttactttaaaccaccactctagttctctgatgcatatttatatagaagttcaagatgac         780
accaaatacaagcaaaaggttaaaggtgccaaaaacagataagcaaagaaacaaaaccta         840
gctaatgaaacagtctagagcctatcaaaaaaaaaaaaaaaacatcgagaaggtgcctag         900
agcggatgggtttcgacaaccctttagctttcatgcatctttttgggaaagggtgaaaaa     960
caccgtcctttaagtcgattgatgcaggcagccttctattgtttgtaagctatcaggaaa         1020
tacaaaattaatagctagttgtcattttaatagttgtagcaagctttgattcttcttttg         1080
tggctgtgacagATGTATGCCGATTACATGACAAGCTTCAGGGAGAACATGAAAGACTTC         1140
```

```
              Met Tyr Ala Asp Tyr Met Thr Ser Phe Arg Glu Asn Met Lys Asp Phe
TTGGATGCTGGTGTTATCGTCGACATTGAAGTGGGACTTGGCCCAGCTGAGGAGATGAGG         1200
Leu Asp Ala Gly Val Ile Val Asp Ile Glu Val Gly Leu Gly Pro Ala Gly Glu Met Arg

TACCCATCATATCCTCAGAGCCACGGATGGTCGTTCCCAGGCATCGGAGAATTCATCgt g   1260
Tyr Pro Ser Tyr Pro Gln Ser His Gly Trp Ser Phe Pro Gly Ile Gly Glu Phe Ile
```

```
agtgtttgtttccaaactaataatctttcctcttctgttccgatcaaatataattttaga           1320
tgtaactcaacatgtgaatatgtgatggccaagtcacgatctacatttagaaaagttttt           1380
tcaggaaacaaacacccaaatgaaaaatgattcttaaaggaaaaaagtgcatggataaaa           1440
tggcagtttcagattaggacaaggcgtggtaaacctgacttgatcatttctgttacccaa           1500
tataccccgcccaatttttgttttttcttattcctcccaaataagacatcatataaact           1560
tgacacattcgtattacaatatgtgaaatatataggatttatctttgcaacttaaatact           1620
taaattgaccttttttattggaaaagactaattttatatatttatggtacaccaaaaatc           1680
caaaatgttttcggcacattgtagtctctatgattcattgaccccacacgtgcggttccc           1740
tcaggcctaaacgtggattgaaagtaggctgcaattttaaaattttaaatttagtgtgtc           1800
aggtcttgaatttaagatcttttgactcggataccatgtaaaactgcaccagacagttca           1860
cccataagctcttgcttatggggaaaggtgggctatgcatttatacttcaacaataaaaa           1920
tagtgatttagcacaaaccttgatgcaaggctagatgacacagatgtgtgtgtgtgtgtg           1980
tgtggggggggggggggggtgatgcacctgaatccgagctcaggaagtttggcactact           2040
tttcccttccgggagaccatatatgttattgctttgagcaaagtatcatagcaaatacaa           2100
gaccttcttaaaatacatgacatgaaatagttaaaacaaatgcacgataatatataccat           2160
tgccattacagaaaaatggctctacttaactgtttgaactaatagtacaaataaaaataa           2220
aattgcagTGCTATGATAAATACCTACAAGCAGACTTCAAAGCAGCAGCAGCGGCGGTCG         2280
```

```
              Cys Tyr Asp Lys Tyr Leu Gln Ala Asp Phe Lys Ala Ala Ala Ala Val G
GCCATCCTGAGTGGGAATTTCCTAACGATGCCGGACAGTACAATGACACTCCCGAGAGAA         2340 ly His Pro Glu Trp Glu Phe Pro Asn Asp Ala Gly Gln Tyr Asn Asp Thr Pro Glu Arg T
CTCAATTCTTCAGGGACAACGGGACATACCTAAGTGAGAAGGGGAGGTTTTTCCTTGCAT          2400 hr Gln Phe Phe Arg Asp Asn Gly Thr Tyr Leu Ser Glu Lys Gly Arg Phe Phe Leu Ala T
GGTACTCCAACAATCTGATCAAGCACGGTGACAGGATCTTGGATGAAGCAAACAAGGTCT          2460
rp Tyr Ser Asn Asn Leu Ile Lys His Gly Asp Arg Ile Leu Asp Glu Ala Asn Lys Val P

TCTTGGGATACAAGGTGCAATTGGCAATCAAGgtataagcactttcatgcctcctaaaga          2520
he Leu Gly Tyr Lys Val Gln Leu Ala Ile Lys
tctcggtttattactacagtagtagataggat  ttgagaaaccatgattcagttgaagt          2580
tgtgtatgataaacaacaaaaaaaatacacaa actatccaggctaagggaactcgcattg         2640
cttaatagctagaatgtaaatgagacatggcc ggccaaataatgtttggttgcagATCTC         2700
                                                          Ile Se TGGCATTCACTGGTGGTACAAGGTTCCAAGCCATGCAGCCGAGCTCACAGCTGGGTACTA          2760
r Gly Ile His Trp Trp Tyr Lys Val Pro Ser His Ala Ala Glu Leu Thr Ala Gly Tyr Ty TAACTTACATGATAGAGACGGCTACAGAACCATAGCACGCATGCTCAAAAGGCACCGTGC         2820
r Asn Leu His Asp Arg Asp Gly Tyr Arg Thr Ile Ala Arg Met Leu Lys Arg His Arg Al TAGCATTAACTTCACTTGCGCGGAGATGAGGGATTCGGAGCAAAGCTCGCAGGCGATGAG         2880
a Ser Ile Asn Phe Thr Cys Ala Glu Met Arg Asp Ser Glu Gln Ser Ser Gln Ala Met Se
```

```
CGCACCAGAAGAACTAGTCCAACAG gtaggtaataacttatgcgttcagatatattacgc          2940
r Ala Pro Glu Glu Leu Val Gln Gln
         ttatatatctacgtatatactatga tggaaacaccttttctttagaaaaggaggcttag   3000
         ccccggcctctgcatcgaaagatgc atacggccatgatgatggaaacacctaaatcactt   3060
         gtcgtcaaaataatttctcag GTGT TGAGTCCTGGATGGAGAGAGGGCCTAAATGTGGCA   3120
                               Val Leu Ser Ala Gly Trp Arg Glu Gly Leu Asn Val Ala TGCGAAAACGCGCTTCCACGATATGATCCAACTGCTTACAACACCATACTCAGGAATGCG              3180
Cys Glu Asn Ala Leu Pro Arg Tyr Asp Pro Thr Ala Tyr Asn Thr Ile Leu Arg Asn Ala AGGCCTCATGGAATCAACCAGAGCGGCCCTCCTGAGCACAAGCTGTTTGGATTCACCTAC              3240
Arg Pro His Gly Ile Asn Gln Ser Gly Pro Pro Glu His Lys Leu Phe Gly Phe Thr Tyr CTTCGGCTGTCGAATCAGCTGGTGGAGGGACAAAACTATGTCAACTTCAAGACCTTTGTC              3300
Leu Arg Leu Ser Asn Gln Leu Val Glu Gly Gln Asn Tyr Val Asn Phe Lys Thr Phe Val GACAGAATGCATGCCAACCTG gttagtgccacaaccacttactaacgcatgtcaaaatt              3360
Asp Arg Met His Ala Asn Leu
     aaacatatacaagaaccattt gttgatttgcaggtgcctattatatactaataatttaat        3420
     tttattgttttcag CCTCGTG ACCCATATGTTGATCCAATGGCGCCTTTGCCAAGATGAG       3480

Pro Arg Asp Pro Tyr Val Asp Pro Met Ala Pro Leu Pro Arg Ser G
GGCCAGAAATATCGATTGAGATGATCCTACAAGCAGCACAGCCAAAACTGCAGCCATTCC              3540 ly Pro Glu Ile Ser Ile Glu Met Ile Leu Gln Ala Ala Gln Pro Lys Leu Gln Pro Phe P
CCTTCCAGGAGCACACCGACCTGCCAGTAGGCCCTACTGGTGGCATGGGTGGGCAGGCTG              3600 ro Phe Gln Glu His Thr Asp Leu Pro Val Gly Pro Thr Gly Gly Met Gly Gly Gln AlaG
AAGGCCCCACCTGTGGCATGGGTGGGCAAGTTAAAGGCCCTACTGGTGGCATGGGTGGGC              3660 lu Gly Pro Thr Cys Gly Met Gly Gly Gln Val Lys Gly Pro Thr Gly Gly Met Gly GlyG
AGGCTGAAGACCCTACTAGTGGCATGGGTGGGGAGCTCCCTGCCACCATGTAATGGAACC              3720 ln Ala Glu Asp Pro Thr Ser Gly Met Gly Gly Glu Leu Pro Ala Thr Met ***
TTTATGATTTACTACCCTTTATGTTGTGTGTGAGTGTGACAGAGAAACCTTTCTCTGCCT              3780

TATTAATAATAAATAAAGCACATCACTTGTGTGTGTTCTGAAAAG                             3825
```

Example 4

Site-Directed Mutagenesis

Site-directed mutagenesis was done with transfer site directed mutagenesis kit (produced by CLONETECH LABORATORIES).

Mutagenesis primers employed were: the nucleotide sequence shown in SEQ. ID. No. 5 in the sequence listing for substitution of Met at 185 position with Leu, the nucleotide sequence shown in SEQ. ID. No. 6 for substitution of Ser at 295 position with Ala and Ile at 297 position with Val, the nucleotide sequence shown in SEQ. ID. No. 7 for substitution of Ser at 350 position with Pro, Ser at 351 position with Pro and Gln at 352 position with Asp, and the nucleotide sequence shown in SEQ. ID. No. 8 for substitution of Ala at 376 position with Ser.

As a selection primer, the nucleotide sequence shown in SEQ. ID. No. 9 in the sequence listing was used.

With the primers described above the site-directed mutagenesis was done to substitute the nucleotides which allows amino acid replacements serving to enhance heat stability of β-amylase to occur, whereby obtaining the gene coding β-amylase consisting of the nucleotide sequence shown in SEQ. ID. No. 2 in the sequence listing.

Example 5

Confirmation of Nucleotide Sequence

When examining the nucleotide sequence of the gene obtained in Example 4, as indicated in SEQ. ID. No.2 in the sequence listing, substitution of A at 1195 position with T, T at 2699 position with G, A at 2705 position with G, AG at 2864 to 2865 positions with CC, T at 2867 position with C, C at 2870 position with G, G at 2872 position with C and G at 3118 position with T were confirmed. Accordingly, the gene which had been subjected to the nucleotide substitution which causes amino acid replacements serving to enhance heat stability of β-amylase consisted of the nucleotide sequence shown in SEQ. ID. No. 2.

Corresponding to the nucleotide sequence described above, amino acid replacements serving to enhance heat stability of β-amylase was done as follows: Met at 185 position with Leu, Set at 295 position with Ala, Ile at 297 position with Val, Set at 350 position with Pro, Set at 351 position with Pro, Gln at 352 position with Asp and Ala at 376 position with Set.

Possibility of Industrial Utilization

According to the present invention, the nucleotides of the barley β-amylase structural genes containing introns were sequenced, and the β-amylase genes, in which amino acid replacements serving to enhance heat stability of β-amylase has occurred, can be constructed. By ligating an appropriate promoter or transcription terminator to such genes to construct recombinant plasmids and introducing the plasmids into barley or other plants, expression of β-amylase in a large amount in barley or expression thereof in other plants and expression of β-amylase having enhanced heat stability in barley or other plants are possible. Accordingly, the present invention can be utilized in breeding of plants and industrial production of β-amylase and can contribute in the technical fields of plant breeding, production of brewed products such as beer, production of distilled liquors, food production and enzyme industry.

We claim:

1. An isolated barley β-amylase structural gene consisting of the nucleotide sequence shown in SEQ. ID. No. 1 in attached sequence listing.

2. An isolated barley β-amylase structural gene consisting of the nucleotide sequence shown in SEQ. ID. No. 2 in attached sequence listing.

3. A plasmid containing the nucleotide sequence shown in SEQ. ID. NO. 1 or 2 in attached sequence listing.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3825 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GATATCCAAC AAACCATTTG AAGTTGTAGA GCATCATCCA TAGCCAGCAT CCACAATGGA      60
GGTGAACGTG AAAGGCAACT ATGTCCAAGT CTACGTCATG CTCCCTGTAA GCTCCATCCA     120
TTCAGACCAA TCGCTGAGAA CCACACACTA AAACTATTTC AAGGATCTAG TGCACACATA     180
TACATTATTG TTGTACATAT AACATTGATA CTTCTTGTAA AACTCTAATT CAAAGGGTGA     240
AGAACAAGAT CTGAGGCCTC AAATGAGTAT TTATTTGTA  CTAACCTTGA CTACACTTCC     300
ATTGTTGAAA TAAATAAATA GCTGGACGCC GTGAGCGTGA ACAACAGGTT CGAGAAGGGC     360
GACGAGCTGA GGGCGCAATT GAGGAAGCTG GTAGAGGCCG GTGTGGATGG TGTCATGGTA     420
GACGTCTGGT GGGGCTTGGT GGAGGGCAAG GGCCCCAAGG CGTATGACTG GTCCGCCTAC     480
AAGCAGTTGT TTGAGCTGGT GCAGAAGGCT GGGCTGAAGC TACAGGCCAT CATGTCGTTC     540
CACCAGTGTG GTGGCAACGT CGGCGACGCC GTCAACATCC AATCCCACA  GTGGGTGCGG     600
GACGTCGGCA CGCGTGATCC CGACATTTTC TACACCGACG GTCACGGGAC TAGGAACATT     660
GAGTACCTCA CTCTTGGAGT TGATAACCAG CCTCTCTTCC ATGGAAGATC TGCCGTCCAG     720
GTTACTTTAA ACCACCACTC TAGTTCTCTG ATGCATATTT ATATAGAAGT TCAAGATGAC     780
ACCAAATACA AGCAAAAGGT TAAAGGTGCC AAAAACAGAT AAGCAAGAA  ACAAAACCTA     840
GCTAATGAAA CAGTCTAGAG CCTATCAAAA AAAAAAAAA  AACATCGAGA AGGTGCCTAG     900
AGCGGATGGG TTTCGACAAC CCTTTAGCTT TCATGCATCT TTTGGGAAA  GGGTGAAAAA     960
CACCGTCCTT TAAGTCGATT GATGCAGGCA GCCTTCTATT GTTTGTAAGC TATCAGGAAA    1020
TACAAAATTA ATAGCTAGTT GTCATTTTAA TAGTTGTAGC AAGCTTTGAT TCTTCTTTTG    1080
TGGCTGTGAC AGATGTATGC CGATTACATG ACAAGCTTCA GGGAGAACAT GAAAGACTTC    1140
TTGGATGCTG GTGTTATCGT CGACATTGAA GTGGGACTTG GCCCAGCTGG AGAGATGAGG    1200
TACCCATCAT ATCCTCAGAG CCACGGATGG TCGTTCCCAG GCATCGGAGA ATTCATCGTG    1260
AGTGTTTGTT TCCAAACTAA TAATCTTTCC TCTTCTGTTC CGATCAAATA TAATTTTAGA    1320
TGTAACTCAA CATGTGAATA TGTGATGGCC AAGTCACGAT CTACATTTAG AAAAGTTTTT    1380
TCAGGAAACA AACACCCAAA TGAAAAATGA TTCTTAAAGG AAAAAAGTGC ATGGATAAAA    1440
TGGCAGTTTC AGATTAGGAC AAGGCGTGGT AAACCTGACT TGATCATTTC TGTTACCCAA    1500
TATACCCCCG CCCAATTTTT GTTTTTTCTT ATTCCTCCCA AATAAGACAT CATATAAACT    1560
TGACACATTC GTATTACAAT ATGTGAAATA TATAGGATTT ATCTTTGCAA CTTAAATACT    1620
TAAATTGACC TTTTTTATTG GAAAGACTA  ATTTATATA  TTTATGGTAC ACCAAAAATC    1680
CAAAATGTTT TCGGCACATT GTAGTCTCTA TGATTCATTG ACCCCACACG TGCGGTTCCC    1740
TCAGGCCTAA ACGTGGATTG AAAGTAGGCT GCAATTTTAA AATTTTAAAT TTAGTGTGTC    1800
```

| | | | | | |
|---|---|---|---|---|---|
| AGGTCTTGAA | TTTAAGATCT | TTTGACTCGG | ATACCATGTA | AAACTGCACC | AGACAGTTCA | 1860 |
| CCCATAAGCT | CTTGCTTATG | GGGAAAGGTG | GGCTATGCAT | TTATACTTCA | ACAATAAAAA | 1920 |
| TAGTGATTTA | GCACAAACCT | TGATGCAAGG | CTAGATGACA | CAGATGTGTG | TGTGTGTGTG | 1980 |
| TGTGGGGGGG | GGGGGGGGGG | TGATGCACCT | GAATCCGAGC | TCAGGAAGTT | GGCACTACT | 2040 |
| TTTCCCTTCC | GGGAGACCAT | ATATGTTATT | GCTTGAGCA | AAGTATCATA | GCAAATACAA | 2100 |
| GACCTTCTTA | AAATACATGA | CATGAAATAG | TTAAACAAA | TGCACGATAA | TATATACCAT | 2160 |
| TGCCATTACA | GAAAAATGGC | TCTACTTAAC | TGTTTGAACT | AATAGTACAA | ATAAAAATAA | 2220 |
| AATTGCAGTG | CTATGATAAA | TACCTACAAG | CAGACTTCAA | AGCAGCAGCA | GCGGCGGTCG | 2280 |
| GCCATCCTGA | GTGGGAATTT | CCTAACGATG | CCGGACAGTA | CAATGACACT | CCCGAGAGAA | 2340 |
| CTCAATTCTT | CAGGGACAAC | GGGACATACC | TAAGTGAGAA | GGGGAGGTTT | TTCCTTGCAT | 2400 |
| GGTACTCCAA | CAATCTGATC | AAGCACGGTG | ACAGGATCTT | GGATGAAGCA | AACAAGGTCT | 2460 |
| TCTTGGGATA | CAAGGTGCAA | TTGGCAATCA | AGGTATAAGC | ACTTCATGC | CTCCTAAAGA | 2520 |
| TCTCGGTTTA | TTACTACAGT | AGTAGATAGG | ATTTGAGAAA | CCATGATTCA | GTTGAGAAGT | 2580 |
| TGTGTATGAT | AAACAACAAA | AAAATACAC | AAACTATCCA | GGCTAAGGGA | ACTCGCATTG | 2640 |
| CTTAATAGCT | AGAATGTAAA | TGAGACATGG | CCGGCCAAAT | AATGTTTGGT | TGCAGATCTC | 2700 |
| TGGCATTCAC | TGGTGGTACA | AGGTTCCAAG | CCATGCAGCC | GAGCTCACAG | CTGGGTACTA | 2760 |
| TAACTTACAT | GATAGAGACG | GCTACAGAAC | CATAGCACGC | ATGCTCAAAA | GGCACCGTGC | 2820 |
| TAGCATTAAC | TTCACTTGCG | CGGAGATGAG | GGATTCGGAG | CAAAGCTCGC | AGGCGATGAG | 2880 |
| CGCACCAGAA | GAACTAGTCC | AACAGGTAGG | TAATAACTTA | TGCGTTCAGA | TATATTACGC | 2940 |
| TTATATATCT | ACGTATATAC | TATGATGGAA | ACACCTTTTT | CTTTAGAAAA | GGAGGCTTAG | 3000 |
| CCCCGGCCTC | TGCATCGAAA | GATGCATACG | GCCATGATGA | TGGAAACACC | TAAATCACTT | 3060 |
| GTCGTCAAAA | TAATTTCTCA | GGTGTTGAGT | GCTGGATGGA | GAGAGGGCCT | AAATGTGGCA | 3120 |
| TGCGAAAACG | CGCTTCCACG | ATATGATCCA | ACTGCTTACA | ACACCATACT | CAGGAATGCG | 3180 |
| AGGCCTCATG | GAATCAACCA | GAGCGGCCCT | CCTGAGCACA | AGCTGTTTGG | ATTCACCTAC | 3240 |
| CTTCGGCTGT | CGAATCAGCT | GGTGGAGGGA | CAAAACTATG | TCAACTTCAA | GACCTTTGTC | 3300 |
| GACAGAATGC | ATGCCAACCT | GGTTAGTGCC | ACAACCACTT | ACTAACGCAT | GTCAAAAATT | 3360 |
| AAACATATAC | AAGAACCATT | TGTTGATTTG | CAGGTGCCTA | TTATATACTA | ATAATTTAAT | 3420 |
| TTTATTGTTT | TCAGCCTCGT | GACCCATATG | TTGATCCAAT | GGCGCCTTTG | CCAAGATCAG | 3480 |
| GGCCAGAAAT | ATCGATTGAG | ATGATCCTAC | AAGCAGCACA | GCCAAAACTG | CAGCCATTCC | 3540 |
| CCTTCCAGGA | GCACACCGAC | CTGCCAGTAG | GCCCTACTGG | TGGCATGGGT | GGCAGGCTG | 3600 |
| AAGGCCCCAC | CTGTGGCATG | GGTGGGCAAG | TTAAAGGCCC | TACTGGTGGC | ATGGGTGGGC | 3660 |
| AGGCTGAAGA | CCCTACTAGT | GGCATGGGTG | GGAGCTCCC | TGCCACCATG | TAATGGAACC | 3720 |
| TTTATGATTT | ACTACCCTTT | ATGTTGTGTG | TGAGTGTGAC | AGAGAAACCT | TTCTCTGCCT | 3780 |
| TATTAATAAT | AAATAAAGCA | CATCACTTGT | GTGTGTTCTG | AAAAG | | 3825 |

( 2 ) INFORMATION FOR SEQ ID NO:2:

( i ) SEQUENCE CHARACTERISTICS:
  ( A ) LENGTH: 3825 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:2:

-continued

```
GATATCCAAC AAACCATTTG AAGTTGTAGA GCATCATCCA TAGCCAGCAT CCACAATGGA    60
GGTGAACGTG AAAGGCAACT ATGTCCAAGT CTACGTCATG CTCCCTGTAA GCTCCATCCA   120
TTCAGACCAA TCGCTGAGAA CCACACACTA AAACTATTTC AAGGATCTAG TGCACACATA   180
TACATTATTG TTGTACATAT AACATTGATA CTTCTTGTAA AACTCTAATT CAAAGGGTGA   240
AGAACAAGAT CTGAGGCCTC AAATGAGTAT TTATTTGTA CTAACCTTGA CTACACTTCC    300
ATTGTTGAAA TAAATAAATA GCTGGACGCC GTGAGCGTGA ACAACAGGTT CGAGAAGGGC   360
GACGAGCTGA GGGCGCAATT GAGGAAGCTG GTAGAGGCCG GTGTGGATGG TGTCATGGTA   420
GACGTCTGGT GGGGCTTGGT GGAGGGCAAG GGCCCCAAGG CGTATGACTG GTCCGCCTAC   480
AAGCAGTTGT TTGAGCTGGT GCAGAAGGCT GGGCTGAAGC TACAGGCCAT CATGTCGTTC   540
CACCAGTGTG GTGGCAACGT CGGCGACGCC GTCAACATCC AATCCCACA GTGGGTGCGG    600
GACGTCGGCA CGCGTGATCC CGACATTTTC TACACCGACG GTCACGGGAC TAGGAACATT   660
GAGTACCTCA CTCTTGGAGT TGATAACCAG CCTCTCTTCC ATGGAAGATC TGCCGTCCAG   720
GTTACTTTAA ACCACCACTC TAGTTCTCTG ATGCATATTT ATATAGAAGT TCAAGATGAC   780
ACCAAATACA AGCAAAAGGT TAAAGGTGCC AAAAACAGAT AAGCAAGAA ACAAAACCTA    840
GCTAATGAAA CAGTCTAGAG CCTATCAAAA AAAAAAAAA AACATCGAGA AGGTGCCTAG    900
AGCGGATGGG TTTCGACAAC CCTTTAGCTT TCATGCATCT TTTTGGGAAA GGGTGAAAAA   960
CACCGTCCTT TAAGTCGATT GATGCAGGCA GCCTTCTATT GTTGTAAGC TATCAGGAAA   1020
TACAAAATTA ATAGCTAGTT GTCATTTTAA TAGTTGTAGC AAGCTTTGAT TCTTCTTTTG   1080
TGGCTGTGAC AGATGTATGC CGATTACATG ACAAGCTTCA GGGAGAACAT GAAAGACTTC   1140
TTGGATGCTG GTGTTATCGT CGACATTGAA GTGGGACTTG GCCCAGCTGG AGAGATGAGG   1200
TACCCATCAT ATCCTCAGAG CCACGGATGG TCGTTCCAG GCATCGGAGA ATTCATCGTG    1260
AGTGTTTGTT TCCAAACTAA TAATCTTTCC TCTTCTGTTC CGATCAAATA TAATTTTAGA   1320
TGTAACTCAA CATGTGAATA TGTGATGGCC AAGTCACGAT CTACATTTAG AAAAGTTTTT   1380
TCAGGAAACA AACACCCAAA TGAAAAATGA TTCTTAAAGG AAAAAGTGC ATGGATAAAA    1440
TGGCAGTTTC AGATTAGGAC AAGGCGTGGT AAACCTGACT TGATCATTTC TGTTACCCAA   1500
TATACCCCCG CCCAATTTTT GTTTTTCTT ATTCCTCCCA AATAAGACAT CATATAAACT    1560
TGACACATTC GTATTACAAT ATGTGAAATA TATAGGATTT ATCTTTGCAA CTTAAATACT   1620
TAAATTGACC TTTTTATTG GAAAAGACTA ATTTTATATA TTTATGGTAC ACCAAAAATC    1680
CAAAATGTTT TCGGCACATT GTAGTCTCTA TGATTCATTG ACCCCACACG TGCGGTTCCC   1740
TCAGGCCTAA ACGTGGATTG AAAGTAGGCT GCAATTTAA AATTTAAAT TTAGTGTGTC     1800
AGGTCTTGAA TTTAAGATCT TTTGACTCGG ATACCATGTA AAACTGCACC AGACAGTTCA   1860
CCCATAAGCT CTTGCTTATG GGGAAAGGTG GGCTATGCAT TTATACTTCA ACAATAAAAA   1920
TAGTGATTTA GCACAAACCT TGATGCAAGG CTAGATGACA CAGATGTGTG TGTGTGTGTG   1980
TGTGGGGGGG GGGGGGGGGG TGATGCACCT GAATCCGAGC TCAGGAAGTT TGGCACTACT   2040
TTTCCCTTCC GGGAGACCAT ATATGTTATT GCTTTGAGCA AGTATCATA GCAAATACAA    2100
GACCTTCTTA AAATACATGA CATGAAATAG TTAAACAAA TGCACGATAA TATATACCAT    2160
TGCCATTACA GAAAAATGGC TCTACTTAAC TGTTTGAACT AATAGTACAA ATAAAAATAA   2220
AATTGCAGTG CTATGATAAA TACCTACAAG CAGACTTCAA AGGAGCAGCA GCGGCGGTCG   2280
GCCATCCTGA GTGGGAATTT CCTAACGATG CCGGACAGTA CAATGACACT CCCGAGAGAA   2340
CTCAATTCTT CAGGGACAAC GGGACATACC TAAGTGAGAA GGGGAGGTTT TTCCTTGCAT   2400
```

```
GGTACTCCAA  CAATCTGATC  AAGCACGGTG  ACAGGATCTT  GGATGAAGCA  AACAAGGTCT      2460

TCTTGGGATA  CAAGGTGCAA  TTGGCAATCA  AGGTATAAGC  ACTTTCATGC  CTCCTAAAGA      2520

TCTCGGTTTA  TTACTACAGT  AGTAGATAGG  ATTTGAGAAA  CCATGATTCA  GTTGAGAAGT      2580

TGTGTATGAT  AAACAACAAA  AAAATACAC   AAACTATCCA  GGCTAAGGGA  ACTCGCATTG      2640

CTTAATAGCT  AGAATGTAAA  TGAGACATGG  CCGGCCAAAT  AATGTTTGGT  TGCAGATCTC      2700

TGGCATTCAC  TGGTGGTACA  AGGTTCCAAG  CCATGCAGCC  GAGCTCACAG  CTGGGTACTA      2760

TAACTTACAT  GATAGAGACG  GCTACAGAAC  CATAGCACGC  ATGCTCAAAA  GGCACCGTGC      2820

TAGCATTAAC  TTCACTTGCG  CGGAGATGAG  GGATTCGGAG  CAAAGCTCGC  AGGCGATGAG      2880

CGCACCAGAA  GAACTAGTCC  AACAGGTAGG  TAATAACTTA  TGCGTTCAGA  TATATTACGC      2940

TTATATATCT  ACGTATATAC  TATGATGGAA  ACACCTTTTT  CTTTAGAAAA  GGAGGCTTAG      3000

CCCCGGCCTC  TGCATCGAAA  GATGCATACG  GCCATGATGA  TGGAAACACC  TAAATCACTT      3060

GTCGTCAAAA  TAATTTCTCA  GGTGTTGAGT  GCTGGATGGA  GAGAGGGCCT  AAATGTGGCA      3120

TGCGAAAACG  CGCTTCCACG  ATATGATCCA  ACTGCTTACA  ACACCATACT  CAGGAATGCG      3180

AGGCCTCATG  GAATCAACCA  GAGCGGCCCT  CCTGAGCACA  AGCTGTTTGG  ATTCACCTAC      3240

CTTCGGCTGT  CGAATCAGCT  GGTGGAGGGA  CAAAACTATG  TCAACTTCAA  GACCTTTGTC      3300

GACAGAATGC  ATGCCAACCT  GGTTAGTGCC  ACAACCACTT  ACTAACGCAT  GTCAAAAATT      3360

AAACATATAC  AAGAACCATT  TGTTGATTTG  CAGGTGCCTA  TTATATACTA  ATAATTTAAT      3420

TTTATTGTTT  TCAGCCTCGT  GACCCATATG  TTGATCCAAT  GGCGCCTTTG  CCAAGATCAG      3480

GGCCAGAAAT  ATCGATTGAG  ATGATCCTAC  AAGCAGCACA  GCCAAAACTG  CAGCCATTCC      3540

CCTTCCAGGA  GCACACCGAC  CTGCCAGTAG  GCCCTACTGG  TGGCATGGGT  GGGCAGGCTG      3600

AAGGCCCCAC  CTGTGGCATG  GGTGGGCAAG  TTAAAGGCCC  TACTGGTGGC  ATGGGTGGGC      3660

AGGCTGAAGA  CCCTACTAGT  GGCATGGGTG  GGGAGCTCCC  TGCCACCATG  TAATGGAACC      3720

TTTATGATTT  ACTACCCTTT  ATGTTGTGTG  TGAGTGTGAC  AGAGAAACCT  TTCTCTGCCT      3780

TATTAATAAT  AAATAAAGCA  CATCACTTGT  GTGTGTTCTG  AAAAG                      3825
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:3:

```
AAGGATCCGA  TATCCAACAA  ACCATTTG                                              28
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:4:

```
AAGGATCCCT  TTTCAGAACA  CACACAAG                                              28
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:5:

```
AGCTGGAGAG TTGAGGTACC C                                    21
```

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:6:

```
GTTGCAGATC GCTGGCGTTC ACTGGTG                              27
```

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:7:

```
AGGGATTCGG AGCAACCCCC GGACGCGATG AGCGCACCA                 39
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:8:

```
CCTAAATGTG TCATGCGAAA A                                    21
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:9:

```
TTGCATGCCT CCAGGTCGAC T                                    21
```

( 2 ) INFORMATION FOR SEQ ID NO:10:

( i ) SEQUENCE CHARACTERISTICS:
        ( A ) LENGTH: 535 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Met Glu Val Asn Val Lys Gly Asn Tyr Val Gln Val Tyr Val Met Leu
 1               5                  10                  15
Pro Leu Asp Ala Val Ser Val Asn Asn Arg Phe Glu Lys Gly Asp Glu
                20                  25                  30
Leu Arg Ala Gln Leu Arg Lys Leu Val Glu Ala Gly Val Asp Gly Val
            35                  40                  45
Met Val Asp Val Trp Trp Gly Leu Val Glu Gly Lys Gly Pro Lys Ala
    50                  55                  60
Tyr Asp Trp Ser Ala Tyr Lys Gln Leu Phe Glu Leu Val Gln Lys Ala
65                  70                  75                  80
Gly Leu Lys Leu Gln Ala Ile Met Ser Phe His Gln Cys Gly Gly Asn
                85                  90                  95
Val Gly Asp Ala Val Asn Ile Pro Ile Pro Gln Trp Val Arg Asp Val
                100                 105                 110
Gly Thr Arg Asp Pro Asp Ile Phe Tyr Thr Asp Gly His Gly Thr Arg
            115                 120                 125
Asn Ile Glu Tyr Leu Thr Leu Gly Val Asp Asn Gln Pro Leu Phe His
    130                 135                 140
Gly Arg Ser Ala Val Gln Met Tyr Ala Asp Tyr Met Thr Ser Phe Arg
145                 150                 155                 160
Glu Asn Met Lys Asp Phe Leu Asp Ala Gly Val Ile Val Asp Ile Glu
                165                 170                 175
Val Gly Leu Gly Pro Ala Gly Glu Met Arg Tyr Pro Ser Tyr Pro Gln
            180                 185                 190
Ser His Gly Trp Ser Phe Pro Gly Ile Gly Glu Phe Ile Cys Tyr Asp
        195                 200                 205
Lys Tyr Leu Gln Ala Asp Phe Lys Ala Ala Ala Ala Ala Val Gly His
    210                 215                 220
Pro Glu Trp Glu Phe Pro Asn Asp Ala Gly Gln Tyr Asn Asp Thr Pro
225                 230                 235                 240
Glu Arg Thr Gln Phe Phe Arg Asp Asn Gly Thr Tyr Leu Ser Glu Lys
                245                 250                 255
Gly Arg Phe Phe Leu Ala Trp Tyr Ser Asn Asn Leu Ile Lys His Gly
            260                 265                 270
Asp Arg Ile Leu Asp Glu Ala Asn Lys Val Phe Leu Gly Tyr Lys Val
        275                 280                 285
Gln Leu Ala Ile Lys Ile Ser Gly Ile His Trp Trp Tyr Lys Val Pro
    290                 295                 300
Ser His Ala Ala Glu Leu Thr Ala Gly Tyr Tyr Asn Leu His Asp Arg
305                 310                 315                 320
Asp Gly Tyr Arg Thr Ile Ala Arg Met Leu Lys Arg His Arg Ala Ser
                325                 330                 335
Ile Asn Phe Thr Cys Ala Glu Met Arg Asp Ser Glu Gln Ser Ser Gln
            340                 345                 350
```

|   |   |   |   |   |   |   |   |   |   |   |   |   |   |   |
|---|---|---|---|---|---|---|---|---|---|---|---|---|---|---|
| Ala | Met | Ser 355 | Ala | Pro | Glu | Glu | Leu 360 | Val | Gln | Gln | Val | Leu 365 | Ser | Ala | Gly |
| Trp | Arg 370 | Glu | Gly | Leu | Asn | Val 375 | Ala | Cys | Glu | Asn | Ala 380 | Leu | Pro | Arg | Tyr |
| Asp 385 | Pro | Thr | Ala | Tyr | Asn 390 | Thr | Ile | Leu | Arg | Asn 395 | Ala | Arg | Pro | His | Gly 400 |
| Ile | Asn | Gln | Ser | Gly 405 | Pro | Pro | Glu | His | Lys 410 | Leu | Phe | Gly | Phe | Thr 415 | Tyr |
| Leu | Arg | Leu | Ser 420 | Asn | Gln | Leu | Val | Glu 425 | Gly | Gln | Asn | Tyr | Val 430 | Asn | Phe |
| Lys | Thr | Phe 435 | Val | Asp | Arg | Met | His 440 | Ala | Asn | Leu | Pro | Arg 445 | Asp | Pro | Tyr |
| Val | Asp 450 | Pro | Met | Ala | Pro | Leu 455 | Pro | Arg | Ser | Gly | Pro 460 | Glu | Ile | Ser | Ile |
| Glu 465 | Met | Ile | Leu | Gln | Ala 470 | Ala | Gln | Pro | Lys | Leu 475 | Gln | Pro | Phe | Pro | Phe 480 |
| Gln | Glu | His | Thr | Asp 485 | Leu | Pro | Val | Gly | Pro 490 | Thr | Gly | Gly | Met | Gly 495 | Gly |
| Gln | Ala | Glu | Gly 500 | Pro | Thr | Cys | Gly | Met 505 | Gly | Gly | Gln | Val | Lys 510 | Gly | Pro |
| Thr | Gly | Gly 515 | Met | Gly | Gly | Gln | Ala 520 | Glu | Asp | Pro | Thr | Ser 525 | Gly | Met | Gly |
| Gly | Glu 530 | Leu | Pro | Ala | Thr | Met 535 |   |   |   |   |   |   |   |   |   |